United States Patent
Hart et al.

(10) Patent No.: US 6,630,144 B1
(45) Date of Patent: Oct. 7, 2003

(54) MONOCLONAL ANTIBODIES TO EBOLA GLYCOPROTEIN

(75) Inventors: Mary K. Hart, Frederick, MD (US); Julie A. Wilson, Frederick, MD (US); Alan L. Schmaljohn, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/650,086

(22) Filed: Aug. 29, 2000

Related U.S. Application Data

(60) Provisional application No. 60/151,505, filed on Aug. 30, 1999.

(51) Int. Cl.[7] .................. A61K 39/42; A61K 39/395
(52) U.S. Cl. ................ 424/159.1; 424/130.1; 424/131.1; 424/139.1; 424/141.1; 424/184.1; 424/186.1
(58) Field of Search ............. 424/130.1, 131.1, 424/133.1, 139.1, 141.1, 159.1, 184.1, 185.1, 186.1

(56) References Cited

U.S. PATENT DOCUMENTS 6,340,463 B1 * 1/2002 Mitchell et al. ......... 424/263.1

FOREIGN PATENT DOCUMENTS

WO    WO 00/00617    1/2000

OTHER PUBLICATIONS

International Search Report for corresponding PCT application PCT/US00/23790, mailed Jan. 11, 2000 (9 pages).

Maruyama, et al., "Recombinant Human Monoclonal Antibodies to Ebola Virus", J. Infectious Diseases, 1999:179 (Suppl. 1):8235–9 (XP–000971336).

Sanchez et al., "Biochemical Analysis of the Secreted and Virion Glycoproteins of Ebola Virus", J. Virology, Aug. 1998, vol. 72, p. 6442–6447.

Xu et al., "Immunization for Ebola Virus infection", Nature Medicine, vol. 4, No. 1, Jan. 1998, p. 37–42.

Volchkov et al., "The envelope glycoprotein of Ebola virus contains as immunosuppressive–like domain similar to oncogenic retroviruses", FEBS Letters, vol. 305, No. 3, Jul. 1992, paes 181–184.

Wilson et al., "Epitopes Involved in Antibody–Mediated Protection from Ebola Virus", Science, vol. 287, Mar. 3, 2000, p. 1664–1666.

* cited by examiner

*Primary Examiner*—James Housel
*Assistant Examiner*—Stacy Brown
(74) *Attorney, Agent, or Firm*—Elizabeth Arwine

(57) ABSTRACT

In this application are described Ebola GP monoclonal antibodies and epitopes recognized by these monoclonal antibodies. Also provided are mixtures of antibodies of the present invention, as well as methods of using individual antibodies or mixtures thereof for the detection, prevention, and/or therapeutical treatment of Ebola virus infections in vitro and in vivo.

20 Claims, 2 Drawing Sheets

FIG. 1

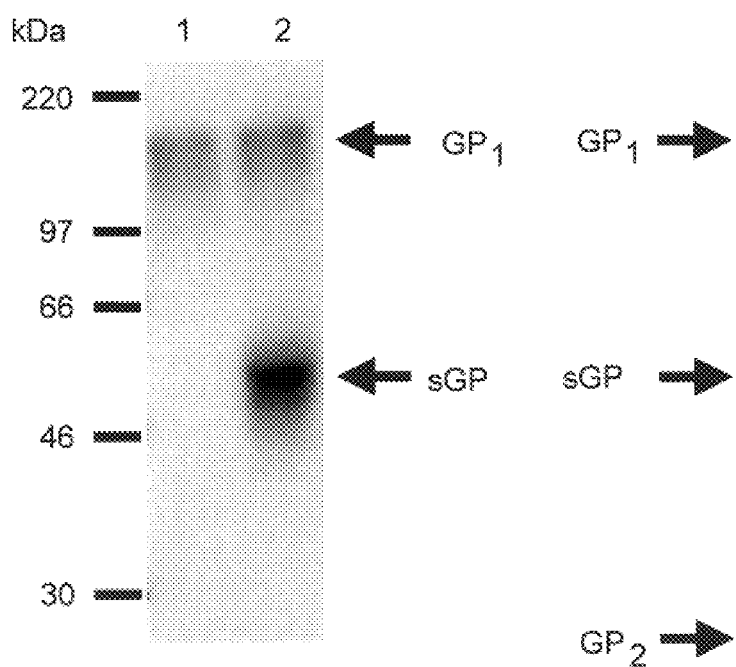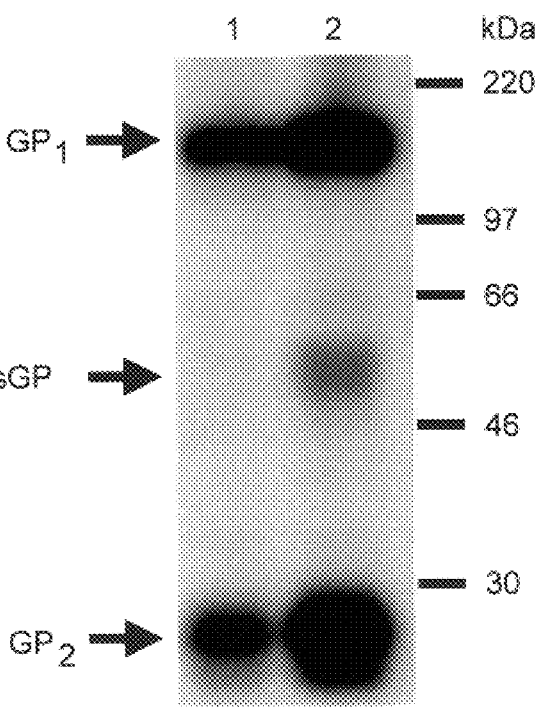

SEQUENCE LISTING

<160> NUMBER OF SEQ ID NOS: 10

<210> SEQ ID NO 1
<211> LENGTH: 2298
<212> TYPE: DNA
<213> ORGANISM: Ebola Zaire

<400> SEQUENCE: 1
atcgataagc tcggaattcg agctcgcccg gggatcctct         40

-continued

```
agagtcgaca acaacacaat gggcgttaca ggaatattgc        80
agttacctcg tgatcgattc aagaggacat cattctttct       120
ttgggtaatt atccttttcc aaagaacatt ttccatccca       160
cttggagtca tccacaatag cacattacag gttagtgatg       200
tcgacaaact agtttgtcgt gacaaactgt catccacaaa       240
tcaattgaga tcagttggac tgaatctcga agggaatgga       280
gtggcaactg acgtgccatc tgcaactaaa agatggggct       320
tcaggtccgg tgtcccacca aaggtggtca attatgaagc       360
tggtgaatgg gctgaaaact gctacaatct tgaaatcaaa       400
aaacctgacg ggagtgagtg tctaccagca gcgccagacg       440
ggattcgggg cttccccccgg tgccggtatg tgcacaaagt      480
atcaggaacg ggaccgtgtg ccggagactt tgccttccat       520
aaagagggtg ctttcttcct gtatgatcga cttgcttcca       560
cagttatcta ccgaggaacg actttcgctg aaggtgtcgt       600
tgcatttctg atactgcccc aagctaagaa ggacttcttc       640
agctcacacc ccttgagaga gccggtcaat gcaacggagg       680
acccgtctag tggctactat tctaccacaa ttagatatca       720
ggctaccggt tttggaacca atgagacaga gtacttgttc       760
gaggttgaca atttgaccta cgtccaactt gaatcaagat       800
tcacaccaca gtttctgctc cagctgaatg agacaatata       840
tacaagtggg aaaaggagca ataccacggg aaaactaatt       880
tggaaggtca accccgaaat tgatacaaca atcggggagt       920
gggccttctg ggaaactaaa aaaaacctca ctagaaaaat       960
tcgcagtgaa gagttgtctt tcacagttgt atcaaacgga      1000
gccaaaaaca tcagtggtca gagtccggcg cgaacttctt      1040
ccgacccagg gaccaacaca acaactgaag accacaaaat      1080
catggcttca gaaaattcct ctgcaatggt tcaagtgcac      1120
agtcaaggaa gggaagctgc agtgtcgcat ctaacaaccc      1160
ttgccacaat ctccacgagt ccccaatccc tcacaaccaa      1200
accaggtccg gacaacagca cccataatac acccgtgtat      1240
aaacttgaca tctctgaggc aactcaagtt gaacaagatc      1280
accgcagaac agacaacgac agcacagcct ccgacactcc      1320
ctctgccacg accgcagccg gaccccaaaa gcagagaac       1360
accaacacga gcaagagcac tgacttcctg gaccccgcca      1400
ccacaacaag tccccaaaac cacagcgaga ccgctggcaa      1440
caacaacact catcaccaag ataccggaga agagagtgcc      1480
agcagcggga agctaggctt aattaccaat actattgctg      1520
gagtcgcagg actgatcaca ggcggggagaa gaactcgaag     1560
agaagcaatt gtcaatgctc aacccaaatg caaccctaat      1600
```

| | |
|---|---|
| ttacattact ggactactca ggatgaaggt gctgcaatcg | 1640 |
| gactggcctg gataccatat ttcgggccag cagccgaggg | 1680 |
| aatttacata gagggctaa tgcacaatca agatggttta | 1720 |
| atctgtgggt tgagacagct ggccaacgag acgactcaag | 1760 |
| ctcttcaact gttcctgaga gccacaactg agctacgcac | 1800 |
| cttttcaatc ctcaaccgta aggcaattga tttcttgctg | 1840 |
| cagcgatggg gcggcacatg ccacattctg ggaccggact | 1880 |
| gctgtatcga accacatgat tggaccaaga acataacaga | 1920 |
| caaaattgat cagattattc atgattttgt tgataaaacc | 1960 |
| cttccggacc aggggacaa tgacaattgg tggacaggat | 2000 |
| ggagacaatg gataccggca ggtattggag ttacaggcgt | 2040 |
| tgtaattgca gttatcgctt tattctgtat atgcaaattt | 2080 |
| gtcttttagt ttttcttcag attgcttcat ggaaaagctc | 2120 |
| agcctcaaat caatgaaacc aggatttaat tatatggatt | 2160 |
| acttgaatct aagattactt gacaaatgat aatataatac | 2200 |
| actggagctt taaacatagc caatgtgatt ctaactcctt | 2240 |
| taaactcaca gttaatcata aacaaggttt gagtcgacct | 2280 |
| gcagccaagc ttatcgat | 2298 |

<210> SEQ ID NO 2
<211> LENGTH: 676
<212> TYPE: PRT
<213> ORGANISM: Ebola Zaire

<400> SEQUENCE: 2

Met Gly Val Thr Gly Ile Leu Gln Leu Pro
 1               5                  10

Arg Asp Arg Phe Lys Arg Thr Ser Phe Phe
                15                  20

Leu Trp Val Ile Ile Leu Phe Gln Arg Thr
                25                  30

Phe Ser Ile Pro Leu Gly Val Ile His Asn
                35                  40

Ser Thr Leu Gln Val Ser Asp Val Asp Lys
                45                  50

Leu Val Cys Arg Asp Lys Leu Ser Ser Thr
                55                  60

Asn Gln Leu Arg Ser Val Gly Leu Asn Leu
                65                  70

Glu Gly Asn Gly Val Ala Thr Asp Val Pro
                75                  80

Ser Ala Thr Lys Arg Trp Gly Phe Arg Ser
                85                  90

Gly Val Pro Pro Lys Val Val Asn Tyr Glu
                95                 100

Ala Gly Glu Trp Ala Glu Asn Cys Tyr Asn
               105                 110

Leu Glu Ile Lys Lys Pro Asp Gly Ser Glu
               115                 120

```
Cys Leu Pro Ala Ala Pro Asp Gly Ile Arg
            125                 130

Gly Phe Pro Arg Cys Arg Tyr Val His Lys
            135                 140

Val Ser Gly Thr Gly Pro Cys Ala Gly Asp
            145                 150

Phe Ala Phe His Lys Glu Gly Ala Phe Phe
            155                 160

Leu Tyr Asp Arg Leu Ala Ser Thr Val Ile
            165                 170

Tyr Arg Gly Thr Thr Phe Ala Glu Gly Val
            175                 180

Val Ala Phe Leu Ile Leu Pro Gln Ala Lys
            185                 190

Lys Asp Phe Phe Ser Ser His Pro Leu Arg
            195                 200

Glu Pro Val Asn Ala Thr Glu Asp Pro Ser
            205                 210

Ser Gly Tyr Tyr Ser Thr Thr Ile Arg Tyr
            215                 220

Gln Ala Thr Gly Phe Gly Thr Asn Glu Thr
            225                 230

Glu Tyr Leu Phe Glu Val Asp Asn Leu Thr
            235                 240

Tyr Val Gln Leu Glu Ser Arg Phe Thr Pro
            245                 250

Gln Phe Leu Leu Gln Leu Asn Glu Thr Ile
            255                 260

Tyr Thr Ser Gly Lys Arg Ser Asn Thr Thr
            265                 270

Gly Lys Leu Ile Trp Lys Val Asn Pro Glu
            275                 280

Ile Asp Thr Thr Ile Gly Glu Trp Ala Phe
            285                 290

Trp Glu Thr Lys Lys Asn Leu Thr Arg Lys
            295                 300

Ile Arg Ser Glu Glu Leu Ser Phe Thr Val
            305                 310

Val Ser Asn Gly Ala Lys Asn Ile Ser Gly
            315                 320

Gln Ser Pro Ala Arg Thr Ser Ser Asp Pro
            325                 330

Gly Thr Asn Thr Thr Thr Glu Asp His Lys
            335                 340

Ile Met Ala Ser Glu Asn Ser Ser Ala Met
            345                 350

Val Gln Val His Ser Gln Gly Arg Glu Ala
            355                 360

Ala Val Ser His Leu Thr Thr Leu Ala Thr
            365                 370

Ile Ser Thr Ser Pro Gln Ser Leu Thr Thr
            375                 380
```

-continued

```
Lys Pro Gly Pro Asp Asn Ser Thr His Asn
                385                 390

Thr Pro Val Tyr Lys Leu Asp Ile Ser Glu
                395                 400

Ala Thr Gln Val Glu Gln His Arg Arg
                405                 410

Thr Asp Asn Asp Ser Thr Ala Ser Asp Thr
                415                 420

Pro Ser Ala Thr Thr Ala Ala Gly Pro Pro
                425                 430

Lys Ala Glu Asn Thr Asn Thr Ser Lys Ser
                435                 440

Thr Asp Phe Leu Asp Pro Ala Thr Thr Thr
                445                 450

Ser Pro Gln Asn His Ser Glu Thr Ala Gly
                455                 460

Asn Asn Asn Thr His His Gln Asp Thr Gly
                465                 470

Glu Glu Ser Ala Ser Ser Gly Lys Leu Gly
                475                 480

Leu Ile Thr Asn Thr Ile Ala Gly Val Ala
                485                 490

Gly Leu Ile Thr Gly Gly Arg Arg Thr Arg
                495                 500

Arg Glu Ala Ile Val Asn Ala Gln Pro Lys
                505                 510

Cys Asn Pro Asn Leu His Tyr Trp Thr Thr
                515                 520

Gln Asp Glu Gly Ala Ala Ile Gly Leu Ala
                525                 530

Trp Ile Pro Tyr Phe Gly Pro Ala Ala Glu
                535                 540

Gly Ile Tyr Ile Glu Gly Leu Met His Asn
                545                 550

Gln Asp Gly Leu Ile Cys Gly Leu Arg Gln
                555                 560

Leu Ala Asn Glu Thr Thr Gln Ala Leu Gln
                565                 570

Leu Phe Leu Arg Ala Thr Thr Glu Leu Arg
                575                 580

Thr Phe Ser Ile Leu Asn Arg Lys Ala Ile
                585                 590

Asp Phe Leu Leu Gln Arg Trp Gly Gly Thr
                595                 600

Cys His Ile Leu Gly Pro Asp Cys Cys Ile
                605                 610

Glu Pro His Asp Trp Thr Lys Asn Ile Thr
                615                 620

Asp Lys Ile Asp Gln Ile Ile His Asp Phe
                625                 630

Val Asp Lys Thr Leu Pro Asp Gln Gly Asp
                635                 640

Asn Asp Asn Trp Trp Thr Gly Trp Arg Gln
```

```
                    645                 650
Trp Ile Pro Ala Gly Ile Gly Val Thr Gly
                    655                 660

Val Val Ile Ala Val Ile Ala Leu Phe Cys
                    665                 670

Ile Cys Lys Phe Val Phe
                    675

<210> SEQ ID NO 3
<211> LENGTH: 105
<212> TYPE: PRT
<213> ORGANISM: Ebola Zaire

<400> SEQUENCE: 3

His Asn Thr Pro Val Tyr Lys Leu Asp Ile
                    5                   10

Ser Glu Ala Thr Gln Val Glu Gln His His
                    15                  20

Arg Arg Thr Asp Asn Asp Ser Thr Ala Ser
                    25                  30

Asp Thr Pro Ser Ala Thr Thr Ala Ala Gly
                    35                  40

Pro Pro Lys Ala Glu Asn Thr Asn Thr Ser
                    45                  50

Lys Ser Thr Asp Phe Leu Asp Pro Ala Thr
                    55                  60

Thr Thr Ser Pro Gln Asn His Ser Glu Thr
                    65                  70

Ala Gly Asn Asn Asn Thr His His Gln Asp
                    75                  80

Thr Gly Glu Glu Ser Asn Ser Ser Gly Lys
                    85                  90

Leu Gly Leu Ile Thr Asn Thr Ile Ala Gly
                    95                  100

Val Ala Gly Leu Ile
                    105

<210> SEQ ID NO 4
<211> LENGTH: 17
<212> TYPE: PRT
<213> ORGANISM: Ebola Zaire

<400> SEQUENCE: 4

Ala Thr Gln Val Glu Gln His His Arg Arg
                    5                   10

Thr Asp Asn Asp Ser Thr Ala
                    15

<210> SEQ ID NO 5
<211> LENGTH: 9
<212> TYPE: PRT
<213> ORGANISM: Ebola Zaire

<400> SEQUENCE: 5

Glu Gln His His Arg Arg Thr Asp Asn
                    5

<210> SEQ ID NO 6
```

-continued

```
<211> LENGTH: 17
<212> TYPE: PRT
<213> ORGANISM: Ebola Zaire

<400> SEQUENCE: 6

His Asn Thr Pro Val Tyr Lys Leu Asp Ile
                 5                   10

Ser Glu Ala Thr Gln Val Glu
                15

<210> SEQ ID NO 7
<211> LENGTH: 9
<212> TYPE: PRT
<213> ORGANISM: Ebola Zaire

<400> SEQUENCE: 7

Val Tyr Lys Leu Asp Ile Ser Glu Ala
                 5

<210> SEQ ID NO 8
<211> LENGTH: 17
<212> TYPE: PRT
<213> ORGANISM: Ebola Zaire

<400> SEQUENCE: 8

Gly Lys Leu Gly Leu Ile Thr Asn Thr Ile
                 5                   10

Ala Gly Val Ala Gly Leu Ile
                15

<210> SEQ ID NO 9
<211> LENGTH: 9
<212> TYPE: PRT
<213> ORGANISM: Ebola Zaire

<400> SEQUENCE: 9

Leu Ile Thr Asn Thr Ile Ala Gly Val
                 5

<210> SEQ ID NO 10
<211> LENGTH: 295
<212> TYPE: PRT
<213> ORGANISM: Ebola Zaire

<400> SEQUENCE: 10

Met Gly Val Thr Gly Ile Leu Gln Leu Pro
 1               5                   10

Arg Asp Arg Phe Lys Arg Thr Ser Phe Phe
                15                   20

Leu Trp Val Ile Ile Leu Phe Gln Arg Thr
                25                   30

Phe Ser Ile Pro Leu Gly Val Ile His Asn
                35                   40

Ser Thr Leu Gln Val Ser Asp Val Asp Lys
                45                   50

Leu Val Cys Arg Asp Lys Leu Ser Ser Thr
                55                   60

Asn Gln Leu Arg Ser Val Gly Leu Asn Leu
                65                   70

Glu Gly Asn Gly Val Ala Thr Asp Val Pro
                75                   80
```

```
Ser Ala Thr Lys Arg Trp Gly Phe Arg Ser
                 85                  90

Gly Val Pro Pro Lys Val Val Asn Tyr Glu
                 95                 100

Ala Gly Glu Trp Ala Glu Asn Cys Tyr Asn
                105                 110

Leu Glu Ile Lys Lys Pro Asp Gly Ser Glu
                115                 120

Cys Leu Pro Ala Ala Pro Asp Gly Ile Arg
                125                 130

Gly Phe Pro Arg Cys Arg Tyr Val His Lys
                135                 140

Val Ser Gly Thr Gly Pro Cys Ala Gly Asp
                145                 150

Phe Ala Phe His Lys Glu Gly Ala Phe Phe
                155                 160

Leu Tyr Asp Arg Leu Ala Ser Thr Val Ile
                165                 170

Tyr Arg Gly Thr Thr Phe Ala Glu Gly Val
                175                 180

Val Ala Phe Leu Ile Leu Pro Gln Ala Lys
                185                 190

Lys Asp Phe Phe Ser Ser His Pro Leu Arg
                195                 200

Glu Pro Val Asn Ala Thr Glu Asp Pro Ser
                205                 210

Ser Gly Tyr Tyr Ser Thr Thr Ile Arg Tyr
                215                 220

Gln Ala Thr Gly Phe Gly Thr Asn Glu Thr
                225                 230

Glu Tyr Leu Phe Glu Val Asp Asn Leu Thr
                235                 240

Tyr Val Gln Leu Glu Ser Arg Phe Thr Pro
                245                 250

Gln Phe Leu Leu Gln Leu Asn Glu Thr Ile
                255                 260

Tyr Thr Ser Gly Lys Arg Ser Asn Thr Thr
                265                 270

Gly Lys Leu Ile Trp Lys Val Asn Pro Glu
                275                 280

Ile Asp Thr Thr Ile Gly Glu Trp Ala Phe
                285                 290

Trp Glu Thr Lys Lys
                295
```

MONOCLONAL ANTIBODIES TO EBOLA GLYCOPROTEIN

This application claims the benefit of provisional application No. 60/151,505 filed Aug. 30, 1999.

Ebola viruses cause acute, lethal hemorrhagic fevers for which no vaccines or treatments currently exist. Knowledge about the immune mechanisms mediating protection is limited. The membrane-anchored GP is the only viral protein known to be on the surfaces of virions and infected cells, and is presumed to be responsible for receptor binding and fusion of the virus with host cells. As a result, Ebola GP may be an important target of protective antibodies. However, the contribution of antibodies to Ebola GP in disease resistance is unclear. Negligible serum titers of neutralizing antibodies in convalescent patients, together with inconsistent results in achieving protection through experimental transfers of immune sera to animals (C. J. Peters and J. W. LeDuc, J. Infect. Dis. 179 (Suppl. 1), ix, 1999; V. V. Mikhailov et al., Vopr. Virusol. 39, 82, 1994) have led to suggestions that antibodies to Ebola GP cannot confer protection to Ebola virus (L. Xu et al., Nature Med. 4, 37, 1998).

The role of anti-GP antibodies in protection is further confounded by the observation that Ebola GP occurs in several forms. The transmembrane glycoprotein of Ebola viruses is unusual in that it is encoded in two open reading frames. Expression of GP occurs when the 2 reading frames are connected by transcriptional or translational editing (Sanchez et al., Proc. Natl. Acad. Sci. USA 93; 3602–3607, 1996; Volchkov et al., Virology 214, 421–430, 1995). The unedited GP mRNA produces a non-structural secreted glycoprotein (sGP) that is synthesized in large amounts early during the course of infection (Volchkov et al., 1995, supra; Sanchez et al., 1996, supra; Sanchez et al., J. Infect. Dis. 179 (suppl. 1, S164, 1999). Following editing, the virion-associated transmembrane glycoprotein is proteolytically processed into 2 disulfide-linked products (Sanchez et al., J. Virol. 72, 6442–6447, 1998). The amino-terminal product is referred to as $GP_1$ (140 kDa) and the carboxy-terminal cleavage product is referred to as $GP_2$ (26 kDa). $GP_1$ and membrane-bound GP, covalently associate to form a monomer of the GP spike found on the surfaces of virions (V. E. Volchkov et al., Proc. Natl. Acad. Sci. U.S.A. 95, 5762, 1998; A. Sanchez et al., J. Virol. 72, 6442, 1998). $GP_1$ is also released from infected cells in a soluble form (V. E. Volchkov. et al., Virology 245, 110, 1998). sGP and $GP_1$ are identical in their first 295 N-terminal amino acids, whereas the remaining 69 C-terminal amino acids of sGP and 206 amino acids of $GP_1$ are encoded by different reading frames. It has been suggested that secreted $GP_1$ or sGP may effectively bind antibodies that might otherwise be protective (Sanchez et al., 1996, supra; Volchkov et al. 1998, supra).

Ebola virus GP is a type I transmembrane glycoprotein. Comparisons of the predicted amino acid sequences for the GPs of the different Ebola virus strains show conservation of amino acids in the amino-terminal and carboxy-terminal regions with a highly variable region in the middle of the protein (Feldmann et al., Virus Res. 24: 1–19, 1992). The GP of Ebola viruses are highly glycosylated and contain both N-linked and O-linked carbohydrates that contribute up to 50% of the molecular weight of the protein. Most of the glycosylation sites are found in the central variable region of GP.

Other studies have also demonstrated limited efficacy of passively transferred polyclonal antibodies in protection against Ebola challenge (Mikhailov et al, 1994, Voprosi Virusologii, 39, 82–84; Jahrling et al., 1996, Arch Virol, 11S, 135–140; Jahrling et al., 1999, J Infect Dis, 179 (Suppl 1), S224–234; Kudoyarova-Zubavichene et al., 1999, J Infect Dis, 179(Suppl 1), S218–223). However, it is difficult to determine the effective therapeutic dose of antibodies in different preparations of polyclonal antibodies. In addition, it is not known if monoclonal antibodies (MAbs) recognizing single epitopes on the Ebola GP are able to effectively neutralize or protect against Ebola virus in vivo.

SUMMARY OF THE INVENTION

This application describes protective GP-specific MAbs. The antibodies are classified into five groups based on competitive binding assays. Individual MAbs in these five groups were protective against Ebola challenge when administered prophylactically or therapeutically. Three of the epitopes bound by protective MAbs are linear sequences on $GP_1$ whereas the other two are conformational epitopes shared between $GP_1$ and sGP. Ten out of 14 MAbs identified in these five competition groups protected BALB/c mice from a lethal challenge with mouse-adapted Ebola Zaire virus when 100 ug of purified MAb was administered 24 hours before challenge (please see Table 3 in Examples below). Similar results were observed in a second mouse strain (C57BL/6). Protection from Ebola challenge decreased when the MAb dose was lowered to 50 or 25 ug (Please see Table 3 and Table 5 in Examples below). For the most effective MAbs, the amount required for protection was within an achievable human therapeutic dose of 3–5 mg/kg.

Some of the MAbs were effective even when administered up to 2 days after challenge (please see Table 3 in Examples below), after significant viral replication had occurred (M. Bray et al., J. Infect. Dis. 178, 651, 1998). None of the MAbs were protective when 100 ug was administered 3 days after challenge, when there are high viral titers (Bray et al., 1998, supra) and possibly irreversible damage of cells and organs.

The ability of the MAbs to inhibit plaque formation by Ebola virus, a standard assay of virus neutralization, did not always predict their protective efficacy. None of the protective MAbs inhibited plaque formation in the absence of complement (please see Table 6 in the Examples below).

Therefore, it is an object of the present invention to provide monoclonal antibodies which protect against Ebola virus and bind to epitopes on the Ebola virus GP. Such antibodies are, for instance, produced by any one of the cell lines deposited under the Budapest Treaty at American Type Culture Collection, Manassas, Va. on Jul. 20, 1999, EGP 13F6-1-2, assigned accession no. PTA-373, EGP6D3-1-1 assigned accession no. PTA-374, EGP 13-C6-1-1 assigned accession no. PTA-375, EGP 6D8-1-2 assigned accession no. PTA-376 and EGP 12B5-1-1 deposited on Jul. 29, 1999 and assigned accession no. PTA-436 (Table 1).

TABLE 1

| Monoclonal | Hybridoma | ATCC accession no. |
| --- | --- | --- |
| MAb 6D8 | EGP 6D8-1-2 | PTA-376 |
| MAb 13F6 | EGP 13F6-1-2 | PTA-373 |
| MAb 12B5 | EGP 12B5-1-1 | PTA-436 |
| MAb 13C6 | EGP 13-C6-1-1 | PTA-375 |
| MAb 6D3. | EGP6D3-1-1 | PTA-374 |

It is another object of the invention to provide for antibodies that are functionally equivalent to the antibodies listed above. These functionally equivalent antibodies substantially share at least one major functional property with an antibody listed above and herein described comprising: binding specificity to Ebola GP, protection against Ebola challenge when administered prophylactically or therapeutically, competition for same binding site on Ebola GP. The antibodies can be of any class such as IgG, IgM, or IgA or any subclass such as IgG1, IgG2a, and other subclasses known in the art. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining an Fab portion and a Fc region from different species.

The monoclonal antibodies of the present invention described below recognize epitopes on Ebola GP (SEQ ID NO: 1 and 2 describe the DNA and amino acid sequence, respectively, of Ebola GP used as an immunogen). Three epitopes are within the sequence extending from 389 to 493 and defined as: HNTPVYKLDISEATQVEQHHRRTDND-STASDTPSATTAAGPPKAENTNTSKSTD-FLDPATTTSPQNHSETAGNNNTHHQDT-GEESASSGKLGLITNTIAGVAGLI (SEQ ID NO:3). More specifically, the cell line EGP 13F6-1-2 produces a monoclonal antibody 13F6 which recognizes and binds to an amino acid sequence of GP corresponding to a region extending from 401 to 417 (SEQ ID NO:4), recognizing an epitope within this region corresponding to Glu-Gln-His-His-Arg-Arg-Thr-Asp-Asn (SEQ ID NO:5). The cell line EGP 6D8-1-2 produces a monoclonal antibody 6D8 which recognizes and binds to an amino acid sequence of GP corresponding to a region extending from 389 to 405 (SEQ ID NO:6), recognizing an epitope within this region corresponding to Val-Tyr-Lys-Leu-Asp-Ile-Ser-Glu-Ala (SEQ ID NO:7). The cell line EGP 12B5-1-1 produces a monoclonal antibody 12B5 which recognizes and binds to an amino acid sequence of GP corresponding to a region extending from 477 to 493 (SEQ ID NO:8), recognizing an epitope within this region corresponding to Leu-Ile-Thr-Asn-Thr-Ile-Ala-Gly-Val (SEQ ID NO:9). The antibodies produced by cell lines EGP 13C6-1-1, 13C6, and EGP 6D3-1-1, 6D3, recognize conformational epitopes in GP sequence that may comprise discontinuous Ebola virus amino acids that are conserved between Zaire and Ivory Coast viruses and found in the 295 amino terminus of the protein (SEQ ID NO:10).

It is another object of the present invention to provide for mixtures of antibodies according to the present invention, as well as to methods of using individual antibodies, or mixtures thereof for the prevention and/or therapeutic treatment of Ebola infections in vitro and in vivo, and/or for improved detection of Ebola infections.

It is yet another object of the present invention to treat or prevent Ebola virus infection by administering a therapeutically or prophylactically effective amount of one antibody of the present invention or a mixture of antibodies of the present invention to a subject in need of such treatment.

It is another object of the present invention to provide passive vaccines for treating or preventing Ebola virus infections comprising a therapeutically or prophylactically effective amount of the antibodies of the present invention which protect against Ebola virus, in combination with a pharmaceutically acceptable carrier or excipient.

It is yet another object of the present invention to provide a method for diagnosis of Ebola virus infection by assaying for the presence of Ebola in a sample using the antibodies of the present invention.

It is still another object of the present invention to provide novel immunoprobes and test kits for detection of Ebola virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to Ebola virus to form an immunological complex and detecting the formation of the immunological complex such that presence or absence of the immunological complex correlates with presence or absence of Ebola virus.

It is another object of the present invention to provide anti-idiotypic antibodies raised against one of the present monoclonal antibodies for use as a vaccine to elicit an active anti-GP response.

It is yet another object of the present invention to provide antigenic epitopes as a component of a Ebola virus vaccine. The epitopes described above comprising SEQ ID NO:3–10, or conservative changes thereof which are still recognized by the antibodies, are useful for actively immunizing a host to elicit production of protective antibodies against Ebola.

BRIEF DESCRIPTION OF THE DRAWINGS

These and other features, aspects, and advantages of the present invention will become better understood with reference to the following description and appended claims, and accompanying drawings where:

Figure 1:
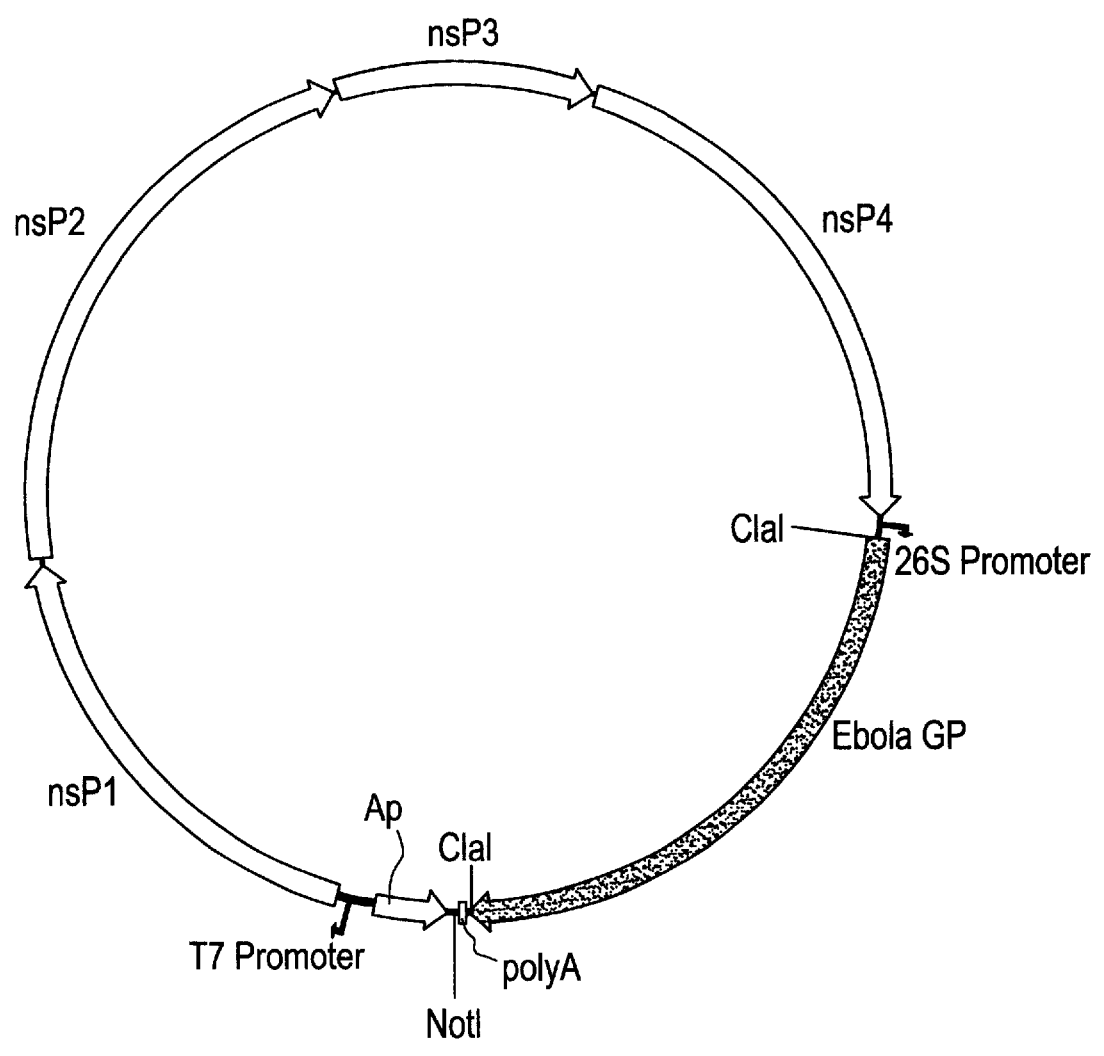

FIG. 1 illustrates the replicon VRegEboGP used make replicon particles EboGP-VRP. The particles were used to vaccinate mice for production of antibodies to Ebola GP.

FIGS. 2A and 2B Immunoprecipitation of $^{35}$S-labeled Ebola GPs from supernatants of Vero cells infected with (A) EboGP-VRPs or (B) Ebola Zaire 1995 virus, with either the MAb 13F6 (Lane 1) or the MAb 13C6 (Lane 2). Both preparations contained secreted $GP_1$ and sGP. Disulfide-linked $GP_1$ and $GP_2$ comprise the spikes on the virions that are also present in the Ebola-infected preparation (B). The immunoprecipitation of GPs with 13F6 was identical to that observed with MAbs 6D8 and 12B5. MAb 6D3 had reactivities identical to MAb 13C6. GP proteins were resolved under reducing conditions on an 11% SDS polyacrylamide gel.

DETAILED DESCRIPTION

In the description that follows, a number of terms used in recombinant DNA, virology and immunology are extensively utilized. In order to provide a clearer and consistent understanding of the specification and claims, including the scope to be given such terms, the following definitions are provided.

"Ebola viruses", members of the family Filoviridae, are associated with outbreaks of highly lethal hemorrhagic fever in humans and nonhuman primates. Human pathogens include Ebola Zaire, Ebola Sudan, and Ebola Ivory Coast. Ebola Reston is a monkey pathogen and is not considered a human pathogen. The natural reservoir of the virus is unknown and there are currently no available vaccines or effective therapeutic treatments for filovirus infections. The genome of Ebola virus consists of a single strand of negative sense RNA that is approximately 19 kb in length. This RNA contains seven sequentially arranged genes that produce 8 mRNAs upon infection. Ebola virions, like virions of other filoviruses, contain seven proteins: a surface glycoprotein (GP), a nucleoprotein (NP), four virion structural proteins (VP40, VP35, VP30, and VP24), and an RNA-dependent RNA polymerase (L) (Feldmann et al.(1992) Virus Res. 24, 1–19; Sanchez et al.,(1993) Virus Res. 29, 215–240; reviewed in Peters et al. (1996) In *Fields Virolooy,* Third ed. pp. 1161–1176. Fields, B. N., Knipe, D. M., Howley, P. M., et al. eds. Lippincott-Raven Publishers, Philadelphia). The glycoprotein of Ebola virus is unusual in that it is encoded in two open reading frames. Transcriptional editing is needed to express the transmembrane form that is incorporated into the virion (Sanchez et al. (1996) *Proc. Natl. Acad. Sci. USA* 93, 3602–3607; Volchkov et al, (1995) *Virology* 214, 421–430). The unedited form produces a nonstructural secreted glycoprotein (sGP) that is synthesized in large amounts early during the course of infection. Little is known about the biological functions of these proteins and it is not known which antigens significantly contribute to protection and should therefore be used to induce an immune response.

The term "antibody" is art-recognized terminology and is intended to include molecules or active fragments of molecules that bind to known antigens. Examples of active fragments of molecules that bind to known antigens include Fab and F(ab')$_2$ fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011–1019 (1982). The term "antibody" also includes bispecific and chimeric antibodies.

The language "monoclonal antibody" is art-recognized terminology. The monoclonal antibodies of the present invention can be prepared using classical cloning and cell fusion techniques. The immunogen (antigen) of interest, Ebola GP protein, is typically administered (e.g. intraperitoneal injection) to wild type or inbred mice (e.g. BALB/c) or transgenic mice which produce desired antibodies, rats, rabbits or other animal species which can produce native or human antibodies. The immunogen can be administered alone, or mixed with adjuvant, or expressed from a vector (VEE replicon vector, vaccinia), or as DNA, or as a fusion protein to induce an immune response. Fusion proteins comprise the peptide against which an immune response is desired coupled to carrier proteins, such as β-galactosidase, glutathione S-transferase, keyhole limpet hemocyanin (KLH), and bovine serum albumin, to name a few. In these cases, the peptides serve as haptens with the carrier proteins. After the animal is boosted, for example, two or more times, the spleen is removed and splenocytes are extracted and fused with myeloma cells using the well-known processes of Kohler and Milstein (*Nature* 256: 495–497 (1975)) and Harlow and Lane (*Antibodies: A Laboratorv Manual* (Cold Spring Harbor Laboratory, New York 1988)). The resulting hybrid cells are then cloned in the conventional manner, e.g. using limiting dilution, and the resulting clones, which produce the desired monoclonal antibodies, cultured.

Monoclonal antibodies raised against Ebola GP as described in the Examples are listed in Table 1 above.

The term "epitope" is art-recognized. It is generally understood by those of skill in the art to refer to the region of an antigen, such as Ebola virus GP, that interacts with an antibody. An epitope of a peptide or protein antigen can be formed by contiguous or noncontinguous amino acid sequences of the antigen. Ebola GP, like many large proteins, contains many epitopes. Examples of Ebola GP epitopes recognized by antibodies of the present invention include the region extending from 389 to 493 and defined as: HNTPVYKLDISEATQVEQHHRRTDND-STASDTPSATTAAGPPKAENTNTSKSTD-FLDPATTTSPQNHSETAGNNNTHHQDT-GEESASSGKLGLITNTIAGVAGLI (SEQ ID NO:3). Continuous epitopes were found within 1) the amino acid sequence of GP corresponding to a region extending from 401 to 417 (SEQ ID NO:4), for example corresponding to Glu-Gln-His-His-Arg-Arg-Thr-Asp-Asn (SEQ ID NO:5), 2) the amino acid sequence of GP corresponding to a region extending from 389 to 405 (SEQ ID NO:6), for example corresponding to Val-Tyr-Lys-Leu-Asp-Ile-Ser-Glu-Ala (SEQ ID NO:7), and 3) the amino acid sequence of GP corresponding to a region extending from 477 to 493 (SEQ ID NO:8), for example Leu-Ile-Thr-Asn-Thr-Ile-Ala-Gly-Val (SEQ ID NO:9). The epitopes or peptides recognized by the antibodies of the present invention and conservative substitutions of these peptides which are still recognized by the antibody are an embodiment of the present invention. These peptides offer a convenient method for eluting GP bound to MAb 6D8, 13F6, or 12B5 on immunoaffinity columns. For example, when an antibody which recognizes the epitope for MAb 6D8, 13F6 or 12B5 is used in an immunoaffinity column to purify Ebola GP, the peptide recognized by the antibody can be added to the immunoaffinity column to elute the Ebola GP. Further truncation of these epitopes may be possible since antigenic epitopes have been reported to be represented by as few as five amino acid residues.

Epitope mapping studies described in this application defined five competition groups of MAbs. Antibodies which compete with the monoclonal antibodies of the present invention for binding to GP are considered to recognize the epitopes of the antibodies and are considered equivalent to the antibodies of the present invention. The MAbs 13C6 and 6D3 recognize conformational epitopes comprising discontinuous Ebola virus amino acids. Antibodies which compete with MAbs 13C6 and 6D3 for binding to Ebola GP are considered to recognize discontinuous epitopes and are considered equivalent to the antibodies of the present invention. Assays for determining whether or not an antibody competes with an antibody of the present invention are known to a person with ordinary skill in the art and are described below. Table 2 below defines functional criteria of each of the monoclonal antibodies identified in the Examples below.

TABLE 2

Epitopes Bound by Ebola GP MAbs.

| Competition Group | Ebola Viruses with Epitope* | Ebola GPs with Epitope† | Epitope Sequence on Ebola GP‡ | Amino Acids§ | |
|---|---|---|---|---|---|
| 1 | Z | GP$_1$ | ATQVEQHHRRTDNDSTA | 401–417 | SEQ ID 4 |
| 2 | Z | GP$_1$ | HNTPVYKLDISEATQVE | 389–405 | SEQ ID 5 |
| 3 | Z | GP$_1$ | GKLGLITNTIAGVAGLI | 477–493 | SEQ ID 8 |
| 4 | Z, IC, S | GP$_1$, sGP | discontinuous | 1–295 | |
| 5 | Z, IC | GP$_1$, sGP | discontinuous | 1–295 | |

*Reactivities of MAbs with Ebola Zaire (Z, isolates from 1976 and 1995), Sudan (S), and Ivory Coast (IC) viruses in ELISA.
†Determined by western blot reactivity with Ebola Zaire 1995 virions or by immunoprecipitation (FIG. 2).
‡MAbs bound two consecutive peptide sequences immobilized on SPOTS membranes. Each peptide was 13 amino acids long and had a 9 amino acid overlap with the preceding and subsequent peptides. Sequences in bold indicate the 9 amino acid overlapping consensus sequence found on both peptides bound by the MAbs. Peptides containing the entire amino acid sequence shown also competed the binding of MAbs to Ebola virions in ELISA.
§Amino acid numbers based on the GP sequence from Genbank (accession number U23187, A. Sanchez, S. G. et al. (1996) Proc. Natl. Acad. Sci., USA 93, 3602).

By further mapping of the binding site of the monoclonal antibodies described in this application other peptides useful as a vaccine or a therapeutic can be predicted. Therefore, in another aspect, this invention relates to a method for identifying protective antigenic epitopes the method comprising (i) reacting a monoclonal antibody described in this application to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease. Peptides defining antigenic protective epitopes can be used in a vaccine as described below and in the Examples.

The epitopes or peptides on Ebola GP to which the monoclonal antibodies bind can constitute all or part of an eventual active vaccine candidate. An active vaccine or therapeutic candidate might comprise these peptide sequences and others. These might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses.

The present invention also pertains to hybridomas producing antibodies which bind to an epitope of Ebola GP. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The present invention still further pertains to a method for detecting Ebola GP in a sample suspected of containing Ebola GP. The method includes contacting the sample with an antibody which binds an epitope of Ebola GP, allowing the antibody to bind to Ebola GP to form an immunological complex, detecting the formation of the immunological complex and correlating the presence or absence of the immunological complex with the presence or absence of Ebola GP in the sample. The sample can be biological, environmental or a food sample.

The language "detecting the formation of the immunological complex" is intended to include discovery of the presence or absence of Ebola GP in a sample. The presence or absence of Ebola GP can be detected using an immunoassay. A number of immunoassays used to detect and/or quantitate antigens are well known to those of ordinary skill in the art. See Harlow and Lane, *Antibodies: A Laboratory Manual* (Cold Spring Harbor Laboratory, New York 1988 555–612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from an Ebola virus vaccinee and a monoclonal antibody of the present invention, are allowed to compete for binding of the antigen. The amount of monoclonal bound is then measured, and a determination is made as to whether the serum contains anti Ebola GP antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (*Clin. Chim. Acta* 70:1–31), and Schurs, A. H. W. M., et al. 1977 (*Clin. Chim Acta* 81:1–40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environmental sample" is meant a sample such as soil and water. Food samples include canned goods, meats, and others.

Yet another aspect of the present invention is a kit for detecting Ebola virus in a biological sample. The kit includes a container holding one or more antibodies which binds an epitope of Ebola GP and instructions for using the antibody for the purpose of binding to Ebola GP to form an immunological complex and detecting the formation of the immunological complex such that the presence or absence of the immunological complex correlates with presence or absence of Ebola virus in the sample. Examples of containers include multiwell plates which allow simultaneous detection of Ebola virus in multiple samples.

As described in greater detail in the examples, the present inventors have isolated five monoclonal antibodies which bind to five epitopes on Ebola GP and display in vitro and/or in vivo Ebola virus protective properties. Significantly, the reactivity of the MAbs is applicable against a broad variety of different wild type and laboratory Ebola strains of different types. Wild type strains include for example Ebola Ivory Coast, Ebola Zaire 1976 (Mayinga isolate), Ebola Zaire 1975, and Ebola Sudan (Boniface). Laboratory strains can be derived from wild type strains and include those which have been passaged or animal adapted strains such as mouse-adapted Ebola.

Given these results, monoclonal antibodies according to the present invention are suitable both as therapeutic and prophylactic agents for treating or preventing Ebola infection in susceptible Ebola-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting Ebola infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before virus can be controlled, and the induced immune response to the MAbs in the subject does not induce "serum sickness" in the subject. Preferably, the MAbs administered exhibit some secondary functions such as binding to Fc receptors of the subject.

Treatment of individuals having Ebola infection may comprise the administration of a therapeutically effective amount of Ebola antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to Ebola GP, or an antibody capable of protecting against Ebola virus in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg–100 pg/kg, 100 pg/kg–500 pg/kg, 500 pg/kg–1 ng/kg, 1 ng/kg–100 ng/kg, 100 ng/kg–500 ng/kg, 500 ng/kg–1 ug/kg, 1 ug/kg–100 ug/kg, 100 ug/kg–500 ug/kg, 500 ug/kg–1 mg/kg, 1 mg/kg–50 mg/kg, 50 mg/kg–100 mg/kg, 100 mg/kg–500 mg/kg, 500 mg/kg–1 g/kg, 1 g/kg–5 g/kg, 5 g/kg–10 g/kg (body weight of recipient), although a lower or higher dosage may be administered.

In a similar approach, another therapeutic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-GP response (Linthicum, D. S. and Farid, N. R., Anti-Idiotypes, Receptors, and Molecular Mimicry (1988), pp. 1–5 and 285–300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding tothe original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., NH$_2$-acetylation or COOH— terminal amidation, to provide additional means for coupling or fusing the peptide to another protein or peptide molecule or to a support.

The antibodies capable of protecting against Ebola virus are intended to be provided to recipient subjects in an amount sufficient to effect a reduction in the Ebola virus infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration maybe in the form of an ingestable liquid or solid formulation.

The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Cell Lines and Viruses

BHK (ATCC CCL 10), Vero 76 (ATCC CRL 1587), and Vero E6 (ATCC CRL 1586) cell lines were maintained in minimal essential medium with Earle's salts, 10% heat-inactivated fetal bovine serum, and 50 ug/ml gentamicin sulfate. Mouse hybridoma cell lines were maintained in Optimem medium (Life Technologies, Rockville, Md.).

A stock of the Zaire strain of Ebola virus originally isolated from a patient in the 1976 Ebola outbreak (isolate Mayinga) and passaged intracerebrally 3 times in suckling mice and 2 times in Vero cells was adapted to adult mice through serial passage in progressively older suckling mice (Bray et al., J. Infect. Dis. 178, 651–661, 1998). A plaque-purified ninth-mouse-passage isolate which was uniformly lethal for adult mice ("mouse-adapted virus") was propagated in Vero E6 cells, aliquotted, and used in all mouse challenge experiments.

Ebola virus antigens used for characterization of monoclonal antibodies were prepared from the following virus seed stocks that were kindly provided by Dr. Peter Jahrling at USAMRIID: the Zaire 1995 strain of Ebola virus isolated from a patient in the 1995 outbreak and passaged 2 times in Vero E6 cells and 2 times in Vero cells; the Zaire 1976 strain of Ebola virus isolated from a patient in the 1976 Ebola outbreak (isolate Mayinga); the Sudan strain of Ebola virus (isolate Boniface) passaged 1 time in a guinea pig, and 3 times in Vero cells; the Ivory Coast strain of Ebola virus obtained from the Center for Disease Control (CDC #807212) and passaged 4 times in Vero E6 cells and 1 time in Vero cells.

Production of Monoclonal Antibodies

Five BALB/c mice were injected subcutaneously at the base of the neck with $2\times10^6$ focus-forming units of Venezuelan equine encephalitis (VEE) virus replicons encoding the glycoprotein (EboGP-VRP) from the Mayinga isolate of the Zaire strain of Ebola virus. EboGP-VRP particles were packaged and purified as described (Pushko et al., 1997 In Vacines 97, pp.253–258. Cold Spring Harbor, N.Y.). Mice received 2 additional subcutaneous injections at one month intervals. ELISA titers to Ebola virus were measured after the third injection and the best two responders received an intravenous injection of $1 \times 10^7$ focus-forming units of Ebola GP replicons (EboGP-VRP) in the tail vein 21 days after the third subcutaneous injection. Three days after the final immunization, spleens were removed and used for fusion to P3X63Ag8:653 myeloma cells as previously described (Stiles et al., Toxicon 29, 1195–1204, 1991). Hybridoma culture supernatants were screened for the presence of antibodies to the Ebola GP by ELISA and by indirect immunofluorescence with fluorescein isothiocyanate (FITC)-conjugated goat anti-mouse antibodies as described below. Positive hybridoma cultures were cloned twice by limiting dilution. Large-scale preparations of MAbs were obtained by culturing hybridoma cell lines in serum-free medium in T150 Integra Celline flasks and purifying the MAbs from the supernatants over Protein G affinity columns (Pharmacia, Piscataway, N.J.). Purified antibodies were dialyzed in PBS and quantitated using a BCA protein assay kit (Pierce, Rockford, Ill.).

Characterization of MAbs ELISA

Enzyme-linked immunosorbent assays (ELISA) were performed essentially as described (Hevey et al., Virology 239: 206–216, 1997). For screening of MAbs, 96-well PVC plates were coated overnight at 4° C. with 0.05 ml of irradiated, sucrose-purified Ebola Zaire 1995 virions (10–20 ug/ml in PBS). For determining the cross-reactivities of the MAbs with other filovirus isolates, PVC plates were coated with either irradiated, sucrose-purified Ebola Zaire 1976 (Mayinga isolate), Ebola Zaire 1995, Ebola Ivory Coast, Ebola Sudan (Boniface). Plates were washed once with PBS containing 0.02% Tween-20 (PBST) and nonspecific binding was blocked by adding 0.25 ml of PBST containing 5% nonfat dry milk (PBSTM) to each well and incubating at room temperature for 1–2 hours. After washing the plates five times with 0.2 ml of PBST, 0.05 ml of undiluted hybridoma culture supernatants or purified MAbs in PBSTM were added to wells containing antigen and plates were incubated for 2 h at room temperature. Bound MAbs were detected using horseradish peroxidase conjugated goat anti-mouse IgA+IgG+IgM (H+L) secondary antibodies and 2,2'-Azinobis-[3-ethylbenzothizoline-6-sulfonic acid] diammonium salt (ABTS) substrate (Kirkegaard and Perry Laboratories, KPL, Gaithersburg, Md.).

Indirect Immunofluroscence Antibody (IFA) Assays

To determine whether the hybridoma cells produced MAbs that recognized either GP or sGP of Ebola virus, Mabs were reacted with Ebola GP-infected BHK cells. BHK cells were infected with EboGP-VRP, or with an irrelevant control replicon expressing the Lassa nucleoprotein, at a multiplicity of infection of 1 to 3 infectious units/cell. Cells were harvested with trypsin 17 h post-infection, washed 2 times in PBS, and diluted to $2 \times 10^5$ cells/ml in PBS. Thirty microliters of the cell suspension was applied to glass spot-slides and the slides were allowed to air dry. Cells were fixed with acetone at −20° C. for 15 min and air-dried. Slides were stored at −70° C. until needed. Twenty microliters of undiluted hybridoma culture supernatants were added, and the slides were incubated for 30 min at room temperature. Excess antibodies were removed from the cells by washing the slides in PBS for 30 min. Twenty microliters of fluorescein-labeled goat anti-mouse IgA+IgG+IgM (H+L) antibodies (50 ug/ml; KPL) was added to the cells and the slides were incubated for 30 min at room temperature. Excess secondary antibodies were removed from the cells by washing the slides for 30 min in PBS. The PBS was removed from the cells, and one drop of mounting medium (KPL) was added to each of the cell spots. Coverslips were added to the slides and the staining patterns were viewed using a fluorescent microscope.

Metabolic Labeling of Ebola Virus Proteins and Radioimunoprecipitation of Ebola GP Proteins Vero E6 cells (75 cm$^2$ flasks) were infected with the Zaire 1995 strain of Ebola virus at a multiplicity of infection of 1 to 3 plaque-forming units/cell. After 24 hours of infection, the growth medium was removed and cells were starved for 30 minutes in medium lacking methionine and cysteine. To label viral proteins, cells were incubated for 24 hours in MEM medium containing 2% heat-inactivated FBS, 0.1 mCi/ml $^{35}$S-labeled methionine and 0.1 mCi/ml $^{35}$S-labeled cysteine. The cell medium was harvested and centrifuged to remove cell debris (15 min at 1500×g) Labeled Ebola virions were obtained by pelleting the clarified supernatant over a 20% sucrose cushion (3 h at 36,000 rpm in a SW41 rotor) and suspending the pelleted virions in Zwittergent lysis buffer. Ebola-infected cell lysates were obtained 24 hours after labeling by lysing infected cell monolayers in Zwittergent Lysis buffer.

To immunoprecipitate Ebola GP from EboGP-VRP-infected cells, Vero cells (75 cm$^2$ flasks) were infected with EboGP-VRP at a multiplicity of infection of 1 to 3 infectious units/cell. After 16 h of infection, cells were starved for 30 minutes in medium lacking methionine and cysteine. To label proteins, cells were incubated for 4 hours in MEM medium containing 2% heat-inactivated FBS, 0.1 mCi/ml $^{35}$S-labeled methionine and 0.1 mCi/ml $^{35}$S-labeled cysteine. Ebola GP mouse MAbs were used to immunoprecipitate Ebola GP proteins from the labeled cell lysates or supernatants.

Western Blot Analysis

Unlabeled Ebola Zaire 1995 virion proteins were resolved on a 10% SDS-polyacrylamide gel and the proteins were transferred to Immobilon-P PVDF membranes. Nonspecific binding sites were blocked by incubating the membranes overnight at 4° C. in PBSTM. Purified MAb (10 ug/ml in PBSTM) were added to the membranes for 1 hour at room temperature. The membranes were then incubated with horseradish peroxidase-conjugated goat anti-mouse IgA+IgG+IgM (H+L) secondary antibodies (1 ug/ml in PBSTM) for 1 hour at room temperature, and the ECL Western blot chemiluminescence kit (Amersham) was used to detect bound MAbs.

Isotype Determination

Antibody subclasses were determined by ELISA. Briefly, 96-well plates were coated with anti-IgG, IgA or IgM heavy-chain specific antibodies (100 ng/well, KPL) and incubated with hybridoma culture supernatants. The subtype of the MAb was detected by using anti-IgG1 (Zymed, South San Francisco, Calif.), IgG2a, IgG2b, IgG3 (Cappel, Durham, N.C.), IgM (KPL), or IgA (Sigma, St. Louis, Mo.) heavy-chain specific antibodies conjugated to alkaline phosphatase.

Biotinylation of MAbs and Competitive Binding Assays

MAbs were biotinylated using an EZ-Link™ Sulfo-NHS-LC-Biotinylation kit (Pierce, Rockford, Ill.) according to the manufacturer's instructions. Competitive binding between unlabeled and biotin-labeled MAbs was performed by reacting a 20-fold excess of unlabeled MAb and 1 to 200 micrograms of biotin-labeled MAb with sucrose-purified, irradiated Ebola Zaire 1995 virus bound to PVC plates. The results of the competition experiment were evaluated by ELISA. The concentrations of biotinylated MAbs used in the competition assays were previously determined to be in the linear portion of their binding curve to Ebola virus antigen.

In vitro Plaque-reduction Neutralization Assay

Plaque assays were performed using confluent Vero-E6 cells. To evaluate the presence of Ebola-neutralizing antibodies, four-fold serial dilutions of MAbs were mixed with 100 pfu of mouse-adapted Ebola virus at 37° C. for 1 h, and used to infect Vero E6 cells. Cells were covered with an agarose overlay (Moe, J. et al. (1981) J. Clin. Microbiol. 13:791–793) and a second overlay containing 5% neutral red solution in PBS or agarose was added 6 days later. Plaques were counted the following day. Endpoint titers were determined to be the last dilution of MAb that reduced the number of plaques by 80% of the control wells.

SPOTS Peptide Analysis

To identify the protein sequences recognized by the MAbs, 166 peptides from the Ebola virus Zaire glycoprotein sequence were synthesized on membranes. Each peptide was 13 amino acids long and had a 9 amino acid overlap with the preceding and subsequent peptides. Peptides were synthesized directly on SPOTS membranes by Genosys, Inc. Two identical membranes were synthesized. Membranes were washed with methanol and then with PBS-0.02% Tween 20 (PBST), blocked overnight at 4° C. in PBST+5% nonfat dry milk (PBSTM), and rinsed in PBST. Ebola virus-specific MAbs were diluted to 5 micrograms/ml in PBSTM milk. Membranes were incubated with 25 ml of MAb for 1.5 h at room temperature, washed for 15 minutes in PBST and then twice more for 5 minutes each. The secondary antibody (affinity purified, peroxidase-labeled goat anti-mouse IgA+IgM+IgG (H+L), Kirkegaard-Perry Labs, Inc. Catalog Number 074-1807, Lot SM055) was diluted 1:1000 in PBSTM and reacted with the membrane for 1.5 hrs at room temperature. The membrane was washed three times in PBST as described above. Lumi GLO chemiluminescent substrate (Kirkegaard Perry Catalog No. 54-61-00, Lot WD033) was prepared according to manufacturer's instructions and added to the membrane for 1 minute at room temperature. The membrane was exposed to Polaroid film using Amersham's ECL camera for various times. Positive spots were white against a black background. Membranes were reused after stripping. Stripping the membrane was performed by rinsing three times for 10 minutes each in 20 ml of MilliQ water, followed by dimethylformamide, and then twice in 20 ml MilliQ water. Three 10 minute washes in 20 ml regeneration buffer A (8M urea, 1% SDS, 0.1% 2-mercaptoethanol) were followed by three 10 minute washes in regeneration buffer B (50% ethanol, 10% acetic acid) and then by two 10 minute washes each in 20 ml methanol followed by PBST. Membranes were then blocked as described above.

Evaluation of MAbs in Mice Administration of MAbs

To determine the prophylactic benefit of Ebola GP MAbs, purified MAbs or combinations of MAbs were injected intraperitoneally into BALB/c or C57BL/6 mice 24 h prior to challenge with mouse-adapted Ebola Zaire virus. For examination of therapeutic effects of MAbs, 100 micrograms of purified antibody, or various concentrations of combined MAbs, were injected intraperitoneally into BALB/c and C57BL/6 mice either 1, 2, or 3 days after challenge with mouse-adapted Ebola Zaire virus. All antibodies were diluted in sterile PBS and 0.2 ml was injected into each mouse.

Ebola Infection of Mice

Mice were transferred to a BSL-4 containment area and challenged by intraperitoneal inoculation of 10 pfu of mouse-adapted Ebola Zaire 1976 virus (approximately 300 times the dose lethal for 50% of adult mice). Virus was diluted in EMEM medium without FBS. Animals were monitored for morbidity and mortality for 28 days post-infection.

Production of EboGP-VRP

The GP gene of Ebola Zaire was previously sequenced by Sanchez et al. (1993, supra) and has been deposited in GenBank (accession number L11365). A plasmid encoding the VEE replicon vector containing a unique ClaI site downstream from the 26S promoter was described previously (Davis, N. L. et al., (1996) J. Virol. 70, 3781–3787; Pushko, P. et al. (1997) Virology 239, 389–401). The Ebbla GP gene from the Ebola Zaire 1976 virus were derived from PS64-based plasmid (Sanchez, A. et al. (1989) Virology 170, 81–91; Sanchez, A. et al. (1993) Virus Res. 29, 215–240). From this plasmid, the BamHI-KpnI (2.4 kb) fragment containing the GP gene was subcloned into a shuttle vector that had been digested with BamHI and EcoRI (Davis et al. (1996) supra; Grieder, F. B. et al. (1995) Virology 206, 994–1006). For cloning of the GP gene, overhanging ends produced by KpnI (in the GP fragment) and EcoRI (in the shuttle vector) were made blunt by incubation with T4 DNA polymerase according to methods known in the art. From the shuttle vector, the GP gene was subcloned as ClaI-fragments into the ClaI site of the replicon clone, resulting in a plasmid encoding the GP gene in place of the VEE structural protein genes downstream from the VEE 26S promoter, resulting in the replicon construct, VRepEboGP.

The Ebola virus GP gene cloned into the VEE replicon was sequenced. Changes in the DNA sequence relative to the sequence published by Sanchez et al. (1993) are described relative to the nucleotide (nt) sequence number from GenBank (accession number L11365).

The nucleotide sequence we obtained for Ebola virus GP (SEQ ID NO:1) differed from the GenBank sequence by a transition from A to G at nt 8023. This resulted in a change in the amino acid sequence from Ile to Val at position 662 (SEQ ID NO: 2).

Transfection of the replicon construct, VRepEboGP along with helper RNAs containing sequences necessary for packaging of the viral replicon transcripts will result in the production of virus-like particles containing replicon RNAs, such as EboGP-VRP. These packaged replicons will infect host cells and initiate a single round of replication resulting in the expression of the Ebola proteins in said infected cells.

EXAMPLE 1

Production and Characterization of Ebola GP MAbs

To obtain MAbs specific for the glycoprotein of Ebola virus, mice were vaccinated with VEE virus replicon particles (VRP) that express Ebola GP (EboGP-VRP). Spleen cells from two mice that were vaccinated with with EboGP-VRP were pooled and fused with P3X63Ag8:653 myeloma cells as described in Methods. In order to detect hybridomas producing antibodies that reacted with the GP of Ebola virus, 1,738 hybridoma supernatants were screened by ELISA for their ability to react with Ebola Zaire virion proteins and by indirect immunofluorescence assay (IFA) for their ability to react with BHK cells infected with EboGP-VRP. The initial screening by ELISA and IFA resulted in 616 positive cultures. Forty of these cultures were chosen for further analysis and were cloned twice by limited dilution. Twenty-seven of the hybridoma cultures continued to react specifically with the Ebola GP throughout the cloning process. The other hybridoma cultures were either lost in the cloning process or produced antibodies that reacted with cellular proteins. Isotype analysis of the MAbs produced by the 27 hybridoma cultures demonstrated that 6 were of the IgG1 subclass, 17 were of the IgG2a subclass, 2 were of the IgG2b subclass, 1 was of the IgG3 subclass, and 1 was an IgA antibody. All of the MAbs produced by these hybridoma cultures reacted with Ebola GP by IFA and 23 of the 27 MAbs reacted with Ebola virions by ELISA. These hybridoma cell lines were cultured in serum-free medium (Life Technologies, Grand Island, N.Y.) in Integra Celline flasks (Integra Biosciences, Inc., Ijamsville, Md.). The IgG MAbs were purified from the supernatants on Protein G affinity columns (Amersham Pharmacia, Piscataway, N.J.), dialyzed in phosphate-buffered saline, and measured using the BCA protein assay (Pierce, Rockford, Ill.).

the MAbs examined, protection from Ebola challenge decreased when the MAb dose was lowered to 50 or 25 ug (Table 3). No protection was observed for any of the mice that received 12.5 ug of MAb (data not shown). For the most effective MAbs, the amount required for protection was within an achievable human therapeutic dose of 3–5 mg/kg.

To determine if the MAbs could be used therapeutically to treat mice that had already been infected with the Ebola virus, 100 ug of purified MAbs were injected into BALB/c or C57BL/6 mice either 1, 2, or 3 days after a lethal challenge with mouse-adapted Ebola Zaire virus. All of the MAbs that demonstrated protective efficacy when administered 1 day prior to challenge were also effective therapeutically when administered 1 day after challenge (Table 3). Some of the MAbs were effective even when administered up to 2 days after challenge (Table 3), after significant viral replication had occurred (M. Bray et al., J.

TABLE 3

Protective Efficacy of Ebola GP Monoclonal Antibodies.

| Competition Group | MAb Designation | Day MAb Administered[1] | BALB/c S/T[2] (100 ug) | BALB/c S/T[2] (50 ug) | BALB/c S/T[2] (25 ug) | C57BL/6 S/T[2] (100 ug) |
|---|---|---|---|---|---|---|
| 1 | 13F6 | −1 | 10/10 | 7/10 | 6/10 | 9/10 |
|   | (IgG2a) | +1 | 10/10 | — | — | 9/10 |
|   |   | +2 | 3/10 | — | — | 2/10 |
| 2 | 6D8 | −1 | 10/10 | 6/10 | 3/10 | 9/10 |
|   | (IgG2a) | +1 | 10/10 | — | — | 9/10 |
|   |   | +2 | 6/10 | — | — | 5/10 |
| 3 | 12B5 | −1 | 6/10 | 2/10 | 0/10 | 6/10 |
|   | (IgG1) | +1 | 8/10 | — | — | 6/10 |
|   |   | +2 | 1/10 | — | — | 1/10 |
| 4 | 13C6 | −1 | 10/10 | 7/10 | 3/10 | 9/10 |
|   | (IgG2a) | +1 | 10/10 | — | — | 10/10 |
|   |   | +2 | 8/10 | — | — | 9/10 |
| 5 | 6D3 | −1 | 9/10 | 6/10 | 2/10 | 8/10 |
|   | (IgG2a) | +1 | 10/10 | — | — | 9/10 |
|   |   | +2 | 9/10 | — | — | 8/10 |
| — | Diluent (PBS) | −1 | 0/10 | — | — | 0/10 |
|   |   | +1 | 0/10 | — | — | 0/10 |
|   |   | +2 | 0/10 | — | — | 0/10 |

[1]Groups of five mice per experiment were injected intraperitoneally with either 100, 50, or 25 ug of MAb in phosphate-buffered saline (PBS) 1 day before (−1), or 1 or 2 days after (+1, +2), challenge with 300 times the dose lethal for 50% of adult mice (10 plaque-forming units) of mouse-adapted Ebola Zaire virus.
[2]S/T, Number of mice that survived challenge/total number challenged.

EXAMPLE 2

Protective Efficacy of Ebola GP MAbs in vivo

In order to determine the protective efficacy of the Ebola GP MAbs, purified MAbs were evaluated for their ability to protect mice from a lethal Ebola challenge (Table 3). In addition, competitive binding assays were performed to determine if the MAbs were recognizing the same epitope or unique epitopes on the Ebola GP (Example 3, Table 4). Fourteen of the MAbs tested in competition assays reacted with 5 different epitopes (Table 5). Ten of these 14 MAbs protected both BALB/c and C57BL/6 mice from a lethal challenge with mouse-adapted Ebola Zaire virus when 100 ug of purified MAb was administered 24 hours before challenge (Tables 3 and 5), demonstrating that antibodies that bind to any one of these Ebola GP epitopes can protect against lethal challenge.

To determine the effective dose of the protective MAbs, BALB/c mice were injected with either 50 ug, 25 ug, or 12.5 ug of purified Ebola GP MAbs 24 h prior to challenge with a lethal dose of mouse-adapted Ebola Zaire virus. For all of the MAbs examined, protection from Ebola challenge Infect. Dis. 178, 651 (1998)). None of the tested MAbs were protective when 100 ug was administered 3 days after challenge (data not shown), when there are high viral titers and possibly irreversible damage of cells and organs.

EXAMPLE 3

Competitive Binding of Ebola GP MAbs

This study identified protective GP-specific MAbs that were classified into five groups on the basis of competitive binding assays. One protective MAb from each of these five different competition groups was chosen for further characterization and was submitted to ATCC as a representative of the competition group. Competitive binding between biotinylated and unlabeled MAbs for the GP of the Ebola Zaire 1995 virus was evaluated by ELISA. The results of the binding assays for the prototypical protective MAb from each competition group are depicted in Table 4. Except for one instance of one-way competition (between the group 4 and 5 MAbs), competition between labeled and unlabeled MAbs was reciprocal.

TABLE 4

Competitive Binding of Ebola GP MAbs

| Biotinylated MAb | Competing Unlabeled MAb | | | | |
|---|---|---|---|---|---|
| | 13F6 | 6D8 | 12B5 | 13C6 | 6D3 |
| 13F6 | 0.3 | 0.8 | 0.5 | 1.0 | 1.2 |
| 6D8 | 0.6 | 0.2 | 0.6 | 0.6 | 0.7 |
| 12B5 | 0.3 | 0.3 | 0.1 | 0.2 | 0.3 |
| 13C6 | 0.6 | 0.7 | 0.6 | 0.1 | 0.5 |
| 6D3 | 0.5 | 0.6 | 0.6 | 0.1 | 0.2 |

Nonprotective MAbs were identified that bound competitively with protective MAbs in groups 1, 4 and 5 (Table 5). All of the antibodies that were completely protective were of the IgG2a subclass, whereas the competing nonprotective MAbs in groups 1 and 4 were of the IgG1 or IgG3 subclasses. Furthermore, the group 3 MAb (12B5), which was only partially protective, was IgG1. Thus, antibody subclass may be an important factor in protection. Murine IgG2a binds complement more effectively than IgG1 or IgG3 and varies in its affinity for different Fc receptors (H. Waldmann, Ann. Rev. Immunol. 7, 407 (1989)). The subclass of the antibody may therefore affect the ability of the MAbs to resolve Ebola infections, for example by lysing infected cells through the classical complement pathway or by binding Fc receptors on cellular effectors of antibody-dependent-cell-mediated cytotoxicity.

TABLE 5

Competition Groups of Ebola GP MAbs

| Competition Group | MAb Designation | MAb Isotype | Protection In Mice |
|---|---|---|---|
| 1 | 13F6 | IgG2a | Yes |
| 1 | 6E3 | IgG1 | No |
| 2 | 6D8 | IgG2a | Yes |
| 2 | 7E10 | IgG2a | Yes |
| 2 | 17E11 | IgG2a | Yes |
| 3 | 12B5 | IgG1 | Yes |
| 4 | 13C6 | IgG2a | Yes |
| 4 | 11H12 | IgG2a | Yes |
| 4 | 9H6 | IgG2a | Yes |
| 4 | 1G8 | IgG2a | Yes |
| 4 | 12E12 | IgG3 | No |
| 5 | 6D3 | IgG2a | Yes |
| 5 | 8C10 | IgG2a | No |
| 5 | 3H8 | IgG2a | No |

Alternatively, the affinity of an antibody for its epitope, possibly influenced by post-translational modifications such as glycosylation, may be an important determinant of protective efficacy. For instance, although group 5 consisted of three IgG2a MAbs, only 6D3 (Table 5) was protective. This MAb bound to Ebola virus at 10-fold lower concentrations than the two nonprotective MAbs (data not shown). In addition, the protective MAb in competition group 1 was more effective than the nonprotective MAb in competition assays (data not shown), suggesting that protective MAbs may have higher affinities for the epitope than nonprotective MAbs.

EXAMPLE 4
Epitopes Bound by Ebola GP MAbs

To further analyze the binding characteristics of the protective MAbs, MAbs were examined by radioimmunoprecipitation, western blot analysis, and peptide-binding assays. MAbs in competition groups 1, 2, and 3 immunoprecipitated GP, but not sGP, from supernatants of cell cultures infected with either Ebola Zaire virus or EboGP-VRPs (FIG. 2), and reacted only with GP1 in western blots (data not shown). The sequences bound by these MAbs were identified by means of synthetic peptides immobilized on membranes and were confirmed with soluble peptides in competition ELISAs (Table 2). These protective MAbs bound linear epitopes within a region of 106 amino acids in the C-terminal portion of GP1. This region is poorly conserved among Ebola viruses and is not shared with sGP. The epitopes bound by MAbs in competition groups 1 and 2 are separated by only three amino acids (Table 2).

In contrast, MAbs in competition groups 4 and 5 immunoprecipitated both GP and sGP from supernatants of infected cells (FIG. 2) but did not bind GP on western blots under reducing conditions or react with any of the synthetic Ebola GP peptides immobilized on membranes (data not shown). These epitopes are therefore discontinuous or require a specific conformation for binding, and are located within the N-terminal 295 amino acids that are identical between sGP and GP1.

EXAMPLE 5
Cross-reactivity of MAbs with Ebola Virus Subtypes

All of the MAbs in this report were generated against the Zaire strain of the Ebola virus. To determine if the MAbs cross-react with the GP of other Ebola strains that are human pathogens, the reactivities of the MAbs with the Zaire 1976, Zaire 1995, Ivory Coast, and Sudan isolates of Ebola virus were compared by ELISA. The Reston strain of the Ebola virus has not been demonstrated to be a human pathogen and was therefore not tested in this report.

When the MAbs were tested for reactivity with the Ebola viruses that are human pathogens, MAbs in competition groups 1, 2, and 3 bound to the two Zaire isolates that have caused the most devastating outbreaks, but did not bind to the Ivory Coast or Sudan viruses (Table 2). All of the MAbs in competition groups 4 and 5 bound to the Ebola Zaire and Ivory Coast viruses. Furthermore, MAbs in competition group 4, but not group 5, also bound to Ebola Sudan (Table 2). These results suggest that it is possible to elicit by vaccination, or produce for therapeutic use, antibodies protective against all Ebola viruses that are pathogenic for humans.

EXAMPLE 6
In vitro Neutralization of Ebola Virus by Ebola GP MAbs

In order to determine if the protective MAbs were able to neutralize Ebola virus in vitro, purified MAbs were evaluated for their ability to inhibit plaque formation by Ebola virus. None of the protective MAbs inhibited plaque formation in the absence of complement (Table 6). In the presence of complement, only MAbs in competition groups 2 and 4 neutralized the virus (80% at 6.25 ug/ml, Table 6). MAb 12B5 (competition group 3) did not reduce the number of plaques, but did reduce plaque size (Table 6), suggesting that it restricted subsequent infection of adjacent cells. These results demonstrated that the ability of the MAbs to inhibit plaque formation by Ebola virus, a standard assay of virus neutralization, did not always predict their protective efficacy.

TABLE 6

In Vitro Neutralization Activity of Ebola GP MAbs.

| MAb Designation | Competition Group | Neutralization w/Complement | Neutralization w/o Complement |
|---|---|---|---|
| 13F6 | 1 | None | None |
| 6D8 | 2 | 6.25 ug/ml | None |
| 12B5 | 3 | None* | None* |
| 13C6 | 4 | 6.25 ug/ml | None |
| 6D3 | 5 | None | None |

*Plaque size was reduced (pinpoint plaques) compared with control plaques. Plaque assays were performed using confluent Vero-E6 cells. To evaluate the presence of Ebola-neutralizing antibodies, four-fold serial dilutions of MAbs (starting at 100 µg/ml) were mixed with 100 pfu of mouse-adapted Ebola virus at 37° C. for 1 h, and used to infect Vero E6 cells. Cells were covered with an agarose overlay (Moe, J. et al. (1981) J. Clin. Microbiol. 13:791–793) and a second overlay containing 5% neutral red solution in PBS or agarose was added 6 days later. Plaques were counted the following day. In some experiments, guinea pig complement (5% final concentration) was added to facilitate antibody-complement lysis of infected cells. Endpoint titers were determined to be the last dilution of MAb that reduced the number of plaques by 80% compared with the control wells.

EXAMPLE 7
Combinations of MAbs Can Reduce the Effective Dose Required for in vivo Protection from Ebola Virus Table 3 demonstrated that MAbs recognizing single epitopes on the Ebola GP were capable of protecting mice from lethal Ebola challenge when 100 ug of Mab was administered either 1 day before or up to 2 days after receiving a lethal dose of Ebola virus. To determine if combinations of MAbs from different competition groups could reduce the effective dose required for protection, MAbs from 3 to 5 different competition groups were mixed and evaluated for their ability to protect BALB/c mice from a lethal challenge with mouse-adapted Ebola Zaire virus. The concentrations of MAbs chosen for these studies were below the concentrations at which the individual MAbs were able to protect all of the mice from death.

Administration of 37.5 ug of a combination of 3 different MAbs (12.5 ug of MAb 13F6, 12.5 ug of MAb 6D8, and 12.5 ug of MAb 13C6) one day prior to Ebola challenge was able to protect 4/5 mice from lethal disease (Table 7A). When the same 3 MAbs were administered at concentrations of either 25 ug or 50 ug of each MAb/mouse (for a total of 75 ug or 150 ug of MAb/mouse, respectively), 100% of the mice were protected from lethal challenge. Therefore, prophylactic administration of a combination of MAbs that recognize different epitopes on the Ebola GP is more efficient than single MAbs at protecting against lethal challenge.

To determine if combinations of MAbs were also effective therapeutically, groups of 5 BALB/c mice were injected with various combinations of MAbs 2 days after a lethal challenge with mouse-adapted Ebola Zaire virus. Combinations of MAbs 13F6, 6D8, and 13C6 were able to protect 4/5 mice when administered at a concentration of 25 ug or 50 ug of each MAb/mouse (Table 7B). When combinations of MAbs 13F6, 6D8, 12B5, 13C6, and 6D3, representing the 5 different competition groups for protective Ebola GP MAbs, were administered at a concentration of either 12.5 ug or 25 ug of each MAb/mouse 2 days after Ebola challenge, all of the mice survived (Table 7B). Therefore, combinations of MAbs which recognize different epitopes on the Ebola GP are effective both prophylactically when administered one day prior to Ebola challenge and therapeutically when administered 2 days after Ebola challenge when significant viral replication has already occurred in the host.

TABLE 7

Protective Efficacy of Combinations of Ebola GP Monoclonal Antibodies

| MAbs Administered | MAb Dose[1] (ug) | Survivors/ Total | MDD[2] |
|---|---|---|---|
| A. Prophylactic Administration (1 Day Prior to Challenge): | | | |
| 13F6, 6D8, and 13C6 | 12.5 of each (37.5 total) | 4/5 | 9* |
| 13F6, 6D8, and 13C6 | 25 of each (75 total) | 5/5 | — |
| 13F6, 6D8, and 13C6 | 50 of each (150 total) | 5/5 | — |
| None (PBS) | — | 0/5 | 6.6 ± 2.0 |
| B. Therapeutic Administration (Day 2 Post-Challenge): | | | |
| 13F6, 6D8, and 13C6 | 25 of each (75 total) | 4/5 | 6* |
| 13F6, 6D8, and 13C6 | 50 of each (150 total) | 4/5 | 7* |
| 13F6, 6D8, 12B5, 13C6 and 6D3 | 12.5 of each (62.5 total) | 5/5 | — |
| 13F6, 6D8, 12B5, 13C6 and 6D3 | 25 of each (125 total) | 5/5 | — |

[1]MAbs were administered intraperitoneally into BALB/c mice either 1 day before or 2 days after challenge with mouse-adapted Ebola Zaire virus.
[2]MDD, Mean Day of Death
*n = 1

This report thus demonstrates that antibodies are a feasible option for the design of safe and standardized treatments for Ebola infections. However, antibody specificity and the ability to neutralize the Ebola virus in vitro cannot be used as sole predictors of protective efficacy. Protection may depend on the proper specificity, isotype, and/or affinity of the antibody.

What is claimed is:

1. An isolated monoclonal antibody which recognizes Ebola virus GP, wherein the epitope that binds or is recognized by said antibody is within SEQ ID NO:6 or SEQ ID NO:8.

2. The antibody according to claim 1, wherein the antibody binds Ebola virus in vitro.

3. The antibody according to claim 1, wherein the antibody immunoprecipitates GP from supernatants or cell lysates of cell cultures infected with Ebola virus.

4. The antibody according to claim 1 wherein said epitope is within SEQ ID NO:6, and is further within SEQ ID NO:7.

5. The antibody according to claim 1 wherein said epitope is within SEQ ID NO:8, and is further within SEQ ID NO:9.

6. The antibody according to claim 1, wherein said antibody is produced by hybridoma cell line EGP 13F6-1-2 with Accession no. PTA-373.

7. An antibody which competes with the antibody of claim 6 for binding to Ebola virus GP.

8. The antibody according to claim 1, wherein said antibody is produced by hybridoma cell line EGP 6D3-1-1 with Accession no. PTA-374.

9. An antibody which competes with the antibody of claim 8 for binding to Ebola virus GP.

10. The antibody according to claim 1, wherein said antibody is produced by hybridoma cell line EGP 13C6-1-1 with Accession no. PTA-375.

11. An antibody which competes with the antibody of claim 10 for binding to Ebola virus GP.

12. The antibody according to claim 1, wherein said antibody is produced by hybridoma cell line EGP 6D8-1-2 with Accession no. PTA-376.

13. An antibody which competes with the antibody of claim 12 for binding to Ebola virus GP.

14. The antibody according to claim 1, wherein said antibody is produced by hybridoma cell line EGP 12B5-1-1 with Accession no. PTA-436.

15. An antibody which competes with the antibody of claim 14 for binding to Ebola virus GP.

16. A mixture comprising Ebola virus antibodies comprising one or more antibodies selected from the group consisting of an antibody produced by hybridoma EGP 13F6-1-2 accession no. PTA 373;

an antibody produced by hybridoma EGP 6D3-1-1 accession no. PTA 374;

an antibody produced by hybridoma EGP 13C6-1-1 accession no. PTA 375;

an antibody produced by hybridoma EGP 6D8-1-2 accession no. PTA 376; and an antibody produced by hybridoma EGP 12B5-1-1 accession no. PTA 436.

17. A monoclonal antibody producing cell line that produces a monoclonal antibody according to claim 1.

18. The cell line according to claim 17, selected from the group consisting of cell line EGP 13F6-1-2 (ATCC accession no. PTA 373), cell line EGP 6D3-1-1 (ATCC accession no. PTA 374), cell line EGP 13C6-1-1 (ATCC accession no. PTA 375), cell line EGP 6D8-1-2 (ATCC accession no. PTA 376), and cell line EGP 12B5-1-1 (ATCC accession no. PTA 436).

19. An antiidiotypic antibody produced from any of the monoclonal antibodies selected from the group consisting of MAb13F6, MAb 6D3, MAb 13C6, MAb 6D8, and MAb 12B5.

20. An antiidiotypic antibody produced from an antibody which competes for binding to GP with an antibody selected from the group consisting of MAb13F6, MAb 6D3, MAb 13C6, MAb 6D8, and MAb 12B5.

* * * * *